United States Patent [19]

Gunn, deceased et al.

[11] Patent Number: 4,517,830

[45] Date of Patent: May 21, 1985

[54] BLOOD VISCOSITY INSTRUMENT

[76] Inventors: Damon M. Gunn, deceased, late of Washington, D.C.; Robert M. Gunn, administrator, 165 Beach Rd., Glencore, Ill. 60022

[21] Appl. No.: 451,529

[22] Filed: Dec. 20, 1982

[51] Int. Cl.³ .................... G01N 11/12; G01N 11/04
[52] U.S. Cl. .......................................... 73/57; 73/54; 73/55
[58] Field of Search ............... 73/54, 55, 57, 64.1; 210/359; 310/359; 128/637, 760, 763, 764, 765, 766

[56] References Cited

U.S. PATENT DOCUMENTS

| | | | |
|---|---|---|---|
| 1,511,998 | 10/1924 | Larson et al. | 73/57 |
| 2,431,378 | 11/1947 | Eitzen et al. | 73/57 |
| 2,439,287 | 4/1948 | Eitzen | 73/57 |
| 2,609,682 | 9/1952 | Eitzen | 73/57 |
| 3,799,342 | 3/1974 | Greenspan | 210/359 X |
| 3,990,295 | 11/1976 | Renovanz et al. | 73/55 |
| 4,083,363 | 4/1978 | Philpot, Jr. | 73/55 X |
| 4,388,823 | 6/1983 | Garnaud et al. | 73/57 |
| 4,427,015 | 1/1984 | Redeaux, Jr. | 128/765 |

OTHER PUBLICATIONS

R. L. Swank et al., Apparatus for Measuring Relative Blood Viscosity, Review of Scientific Inst., 1954.

Primary Examiner—Howard A. Birmiel
Assistant Examiner—Hezron E. Williams
Attorney, Agent, or Firm—Jim Zegeer

[57] ABSTRACT

Apparatus for detecting the viscosity of blood comprises a hypodermic syringe including a transparent hollow tube, a needle secured to one end of the tube and a plunger in the tube for creating a vacuum for extracting a predetermined volume of blood and depositing the blood in the transparent hollow tube for immediately performing internal viscosity measurement without substantial change in temperature and without any chemical change (e.g. exidation) in the blood sample. An apertured weight member within the transparent hollow tube is movable by gravity at a rate which is a function of the viscosity of the blood and indicia means, visible on the side of the transparent tube indicates the rate of movement of the apertured weight member through the predetermined volume of blood as a measure of the viscosity of the blood in the tube.

10 Claims, 8 Drawing Figures

BLOOD VISCOSITY INSTRUMENT

BACKGROUND AND BRIEF DESCRIPTION OF THE INVENTION

The present invention is for the measurement of the viscosity of blood freshly drawn from the circulatory system of mammals, particularly human beings.

It is interesting that not much has been done to measure and study the viscosity of the blood in the human system particularly immediately after the blood has been drawn. One measurement system is disclosed in Seitz U.S. Pat. No. 3,635,678 wherein blood is drawn and placed in a test tube and then a member suspended in the tube and which changes position when the sample achieves a predetermined degree of viscosity. The change in position is sensed and is used in the determination of the time required for the blood to form a fibrin clot in a plasma or to effect particular reaction causing solidification of congealing of the sample. This clot timing system is rather complex and expensive and the blood in the test tube is subject to oxidation and temperature change so that it is not an accurate measure of the viscosity of the blood flowing in the circulatory system of the human.

Of course, drawing blood is a relatively recent innovation and the study of blood is becoming more of a science (called the science of hemotology). Viscosity may change (e.g. "thinning" and "thickening" of blood) under certain conditions but such changes have not been given the attention that it merits. It is to be understood that by viscosity, it is meant the viscousness or flowability, or as all are well acquainted, with an automobile engine the necessity to have lubricating oil that does not get too thin when hot, nor too thick when cold, and thus a low viscosity when hot, and a high viscosity when cold. The term "viscosity" then is directed towards the viscousness of liquid blood. The present invention is directed toward the determination of the viscosity (viscounsness) of blood (almost in vivos) and towards a single instrument for study of changes in viscosity with, age of a person, or with fatigue, or with time of the day (the blood may change viscosity during the day) according to the various chemicals that may be in the blood, as for example, aspirin, prostacycline or other blood thinning agents and the invention is directed towards a single instrument and method for improving the study of the speed which aspirin gets into the blood stream and the effectiveness thereof in alleviating heart conditions and heart attacks and strokes. Moreover, the evaluation of certain hormones in the blood and the effect thereof and how viscosity affects surgery in bleeding may also be studied by use of the present invention.

Of course, the technology of high and low blood pressure and of taking the blood pressure (BP) is common. Almost every doctor wants to know why should he give up his old practice of reading the amount of pressure that is necessary to restrict the flow of blood in favor of a different procedure for establishing the pressure of the blood itself. A more detailed analysis of the procedure of taking blood pressure shows that from a point of view of hydraulics, the taking of blood pressures leaves a lot to be desired. As to the condition of blood which may be causing the change or an increase in or decrease in blood pressure. Blood pressure may be affected by the strength or collapsibility of the blood vessel being constricted, it may vary according to the viscosity of the circulating blood, a thick blood would be less easily constricted than a thin blood and the passage of blood through the tissue by the capillaries or osmosis is effected again by the thickness or thinness of the blood e.g. more viscous, highly viscous or less viscous blood. Finally, the relation of the heart's ability to exert pressure by its pumping action may be governed somewhat by the viscousness of the blood. Thus, the ability of the blood to circulate freely or be slowed or stopped because of a stroke is evident. There are many ailments which are affected by the blood circulation such that determining the viscosity may lead to better diagnosis thereof.

Thus, the basic object of the present invention is to provide a simple blood viscosity measuring device so as to provide more diagnostic information for the physician in diagnosing ailments.

The invention may be used to develop standardization of terminology for use in description of the blood's viscosity over critical ranges. Finally, it is believed that dehydration, which comes from over exertion or impellation or anything which tends to make a person over exert, can be a fore runner of a stroke, especially if the heart has not been conditioned for some time to handle thicker or more viscous blood. If a person's heart is conditioned to handle more viscous or thicker blood, it mitigates the changes of a stroke.

Thus, the present invention is directed towards measuring the viscosity of blood from living organisms. The differentiation is further defined in applying the viscosity measurement of the blood and primarily as near as possible to a state of circulation in the body inasmuch as blood coagulates quickly if it is exposed to air and oxidizes. It is necessary that the measurement be done by apparatus which is simple and can be administered or operated right on the patient as the patient is prostrate or sitting as is done by an ordinary trained nurse in taking the blood pressure or in taking a blood sample. In fact, an object of the present invention is to make the measurement of the blood viscosity performed substantially at the time that a blood sample is taken from the patient and that that same blood sample upon which the viscosity measurements are made can be utilized in running the usual blood tests in a laboratory to provide various chemical analysis of the blood. The present invention therefore provides a dual purpose device in that it can be used for the measurement of viscosity as well as for the extraction of blood from the patient for normal chemical analysis in a laboratory.

There are, of course, devices for ascertaining the oxygen in the blood after a sample is taken of the blood and a dilutant is added so that it does not coagulate. Falling weight viscosity meters are well known in the art, see Eitzen et al U.S. Pat. No. 2,431,378 and Eitzen U.S. Pat. No. 2,439,287, incorporated herein by reference. The well known Saybolt viscosimeter is another example where flow of predetermined quantity, through a tube is timed to give a measurement which is proportional to the coefficient of viscosity. As indicated above, Seitz U.S. Pat. No. 3,635,678 is directed to a clot timing system and method and is dependent upon the coagulation of the blood for a reading. The present invention depends upon taking a blood viscosity measurement almost as soon as the blood has been extracted, and while it is still at substantially the same body temperature as the patient and before any coagulation and/or oxidation has taken place and, in fact, the blood is sealed in a syringe type instrument and the viscosity measurement made so as to obtain the viscosity reading of the blood almost as soon as it has been isolated from the veins.

If the blood has a high viscosity, then it won't circulate as well but that fact may not show up in the blood pressure reading. It is advantageous therefore to take the blood viscosity measurement at the same time that the blood pressure reading is taken so as to permit the physician to use any correlated changes in viscosity and blood pressure in his diagnosis. Thus, patients charts should also have provisions for recording the blood viscosity measurement. If the artery which carries the blood is strong, it does not compress easily to maintain circulation. The present device can be useful in making tests that would least give an alarm that a danger of stroke exists and may be corrected by the use of a blood thinning agent (e.g. prosteydine). Furthermore, the device can be useful in telling whether or not drugs or other additives tend to lower or raise the viscosity of the blood by testing individuals to whom the drug or additive has been administered. Patients taking an aspirin a day so as to avoid stroke are believed to have the viscosity of the blood changed by aspirin and/or other viscosity blood thinning agents.

Thus, the basic objectives of the invention are achieved by the integral combination providing a blood extracting means such as an hypodermic syringe and a viscosity measuring structure, which, in the preferred embodiment is a falling weight to provide for measuring the viscosity of blood almost immediately upon being extracted from the patient. A restricted orifice in the falling weight member provides for relative flow of the blood and hence shear effects.

The above and other objects, advantages and features of the invention will become more apparent when considered with the following specification taken in conjuction with the accompanying drawings wherein:

FIG. 1 is a sectional view of a blood viscosity measuring instrument incorporating the invention, FIG. 2 is a partial sectional view of a modification of the invention showing the detailed structure of the Teflon coated weight and check valve structure, FIG. 3 is a sectional view of a further modification of the invention showing the hollow plunger rod handle for measuring the pressure of the piston falling on the blood, FIG. 4 illustrates a stand timer in the practice of the invention, and FIGS. 5a, 5b, 5c and 5d diagrammatically illustrate other forms of viscosity measuring instruments which may be used in the invention.

DETAILED DESCRIPTION OF THE INVENTION

Figure 1:
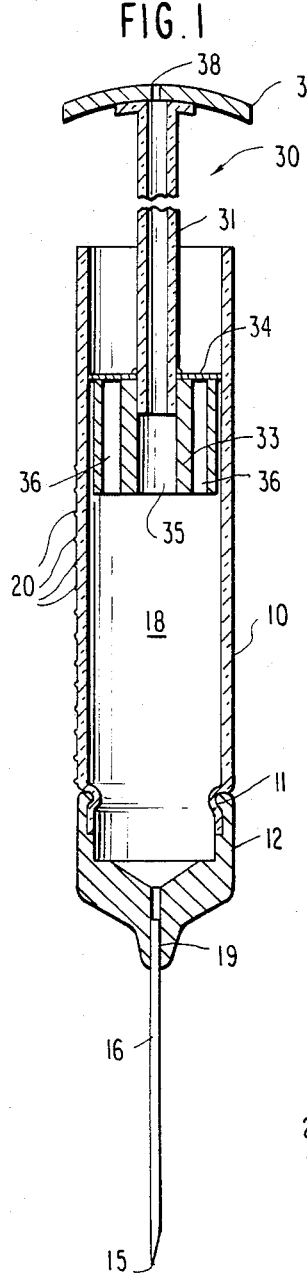
Figure 2:
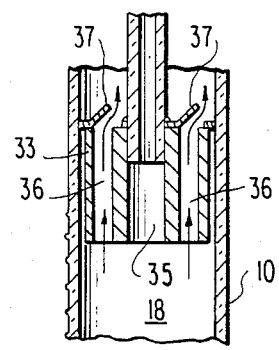
Figure 5A:
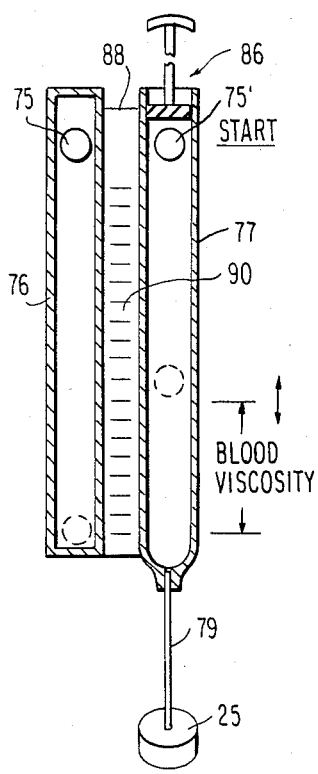
Figure 5B:
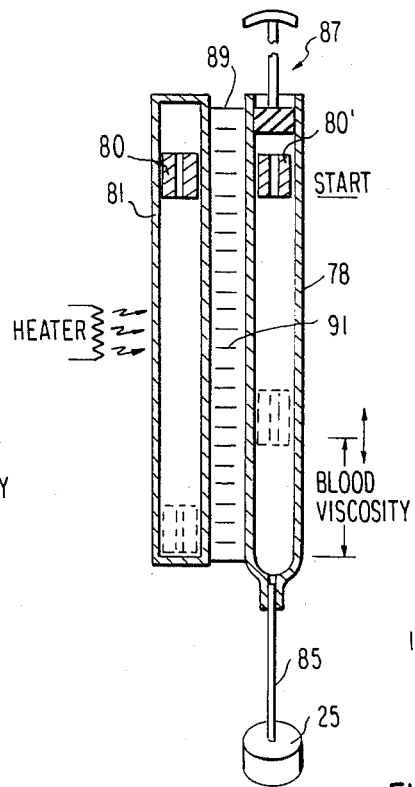

Referring to FIG. 1, a hollow glass tube 10 has an annular rib or groove 11 formed in one end thereof which coacts with a metal closure ferrule 12 which carries a metal hypodermic needle 14, which is a typical hypodermic syringe needle having a sharpened lower end 15 and a hollow central bore 16. Central bore 16 communicates through to the interior chamber 18 of the glass tube 10. Needle 14 is secured to closure member 12 by conventional crimping 19. Indicia 20 are graduations forming a scale which, in association with a stop watch, or other timing means, gives an indication of the viscosity of the blood as will be discussed more fully hereafter. However, it will be appreciated that as shown in FIGS. 5a and 5b, the scale is graduated and may be compared to water as a reference (e.g. as in the master or reference tubes of the Eitzen patents referred to above) so that the viscousness of the blood, whether to be greater or less than water will be measured in terms of distilled water at room temperature of about 70° F. It will be appreciated that since the body temperature is normally 98.6, this standard temperature could be transposed to that temperature e.g. a distilled water at body temperature of the patient being utilized as a standardized gauge from which to determine whether the blood viscosity is above or below that medium. Prior to taking any blood sample the tubes are preferably maintained at normal body temperature (98.6° F. for humans) so that there will be no change in the temperature of the blood sample.

While the tube 10 is shown as being generally cylindrical, it will be appreciated that this is for ease of manufacturing and the tube could be square, oval or any other cross section.

Figure 3:
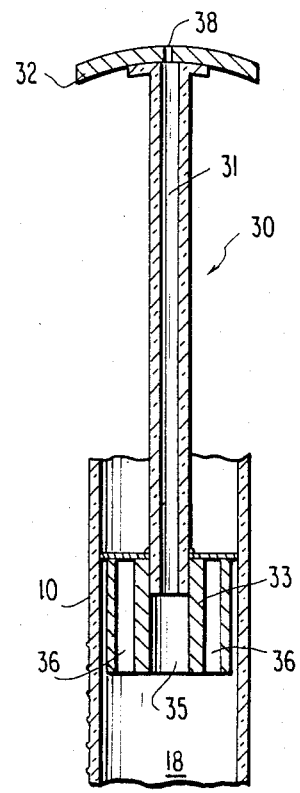

As shown in FIG. 3, plunger 30 has a hollow handle 31 secured to pull member or knob 32 and piston 33 secured to the opposite end of rod 31. Piston 33 is a Teflon coated weight which is several thousandths (2 to 3 thousandths) smaller in diameter than the tube 10. A low friction seal-check valve element 34 which is formed of Teflon or other low friction material seals against the interior surfaces or walls of tube 10 when plunger 30 is withdrawn so as to create a vacuum and thereby draw blood through needle 15. Hollow tube 31 is in open communication through passageway 35 in piston 33 which, as described above, is Teflon coated, so that the level of blood in hollow rod 31 is a measure of the pressure of the piston 33 falling on the blood and should be constant. Passageways 36 in piston 33 are provided to permit the blood to flow at a constant rate therethrough and Teflon check valve seal element 34 has a plurality of flaps 37 which are aligned with passageways 36. Thus, the peripheral edges of seal-check valve element 34 engage the inner walls of tube 10, the flapper check valve elements 37 are drawn to seal the space in chamber 10. The user's thumb seals the passageway 36 to handle rod 31 so that a vacuum is created in chamber 18. Thus, as the piston is withdrawn from cylinder 10, a vacuum is formed thereby withdrawing blood from the patient and into the space 18 in tube 10.

As soon as the blood has been withdrawn, it is mounted in stand 40 and piston 33, which, as indicated above, is Teflon coated, is allowed to freely fall through the blood in chamber 18. The nurse or user of the instrument begins to time the period of time it takes for the weighted piston and rod to fall through a selected distance on the graudated scale. Thus time, correlated with the graduations on the scale are a measure of the viscosity of the blood. It will be appreciated that timer or stop watch 28 may be mounted as on the stand and started and stopped and the stop watch calibrated in terms of blood viscosity. Thus, if it takes an X period of seconds for the weighted member constituted by piston 33 to travel through the blood, this can be calibrated in terms of viscosity e.g. Saybolt seconds.

Figure 4:
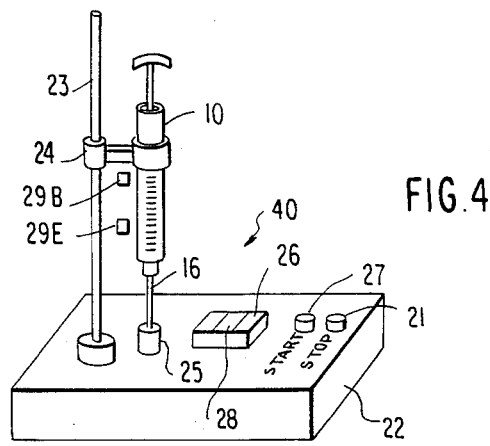

As shown in FIG. 4, a stand 40 has a base 22 and vertical post 23 carrying tube holder 24 for tube body 10. The bore 16 is blocked by insertion of the needle end 15 into a cork or rubber block 25. After a predetermined quantity of blood has been drawn into tube body 10, and the needle end 15 inserted into block 25, the tube is placed in the yoke of holder 24 and timer 26 started by pressing start button 27. As soon as the apertured weight reaches the bottom of tube 10, the stop button is depressed. The display 28 can be in seconds and fractions of seconds which can be converted to standard units of viscosity e.g. Saybolt or the display can be calibrated in units of viscosity. Instead of visually determining the start and stop of the falling weight and to eliminate accelleration effects, a photocell detector 29B and 29E can be connected to timer 26 and be used to determine the time (and hence viscosity) it takes for the weight to pass a predetermined amount of blood.

As shown in FIGS. 5a and 5b, respectively, the rate of passage of a weighted ball 75, 75' or apertured weight members 80, 80' are compared to the same element in a liquid reference of known viscosity e.g. distilled water, at 98.6° F. In these embodiments, reference tubes 76 and 81 containing the same predetermined quantity of reference liquid, are secured in parallel relation with blood sample tubes 77 and 78, respectively, which have their respective needles 79 and 85, and operating plunger handles 86 and 87. In these embodiments, after extracting the sample, the device is held vertical to allow the weight members to travel to the opposite end and then turned or oriented in the opposite vertical direction to permit gravity effects to move the weight relative to the blood. Scales 88 and 89 have indicia 90 and 91 so that by measuring the difference in time it takes for the weighted members to traverse the predetermined volumes of the reference liquid and blood sample, the viscosity of the blood sample is determined. The position of the ball or aperture weight member in the blood sample at the instant the ball or weight member in the reference tube reaches the bottom, or in other words has traversed the predetermined volume of reference liquid, is translated by the scale 88 or to the viscosity of the blood sample.

Figure 5C:
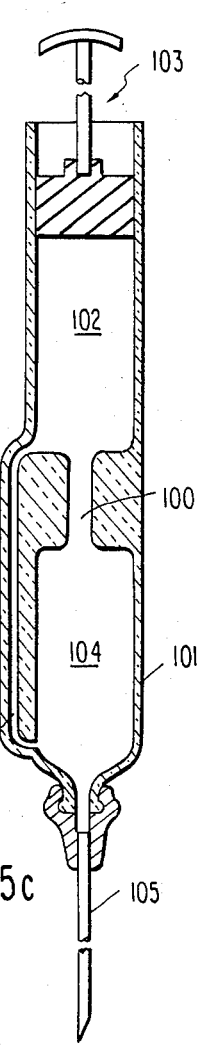

In the modifications shown in FIG. 5c, instead of a falling weight, a constricted passage 100 is formed internally in tube body 101 forming two chamber halves, the upper half 102 containing a piston and plunger 103 and the lower half 104 carrying the hypodermic needle 105. An air relief passage 106 (in addition to air through needle 105) is provided so that after the blood sample is drawn into lower chamber half 104, and the unit is turned so that chamber half 102 is vertically below chamber half 104, blood will flow to the upper chamber half 102. The time it takes for the predetermined quantity of blood in the chamber half 104 to flow through the constricted passage 100 is a function of the viscosity of the blood sample.

Figure 5D:
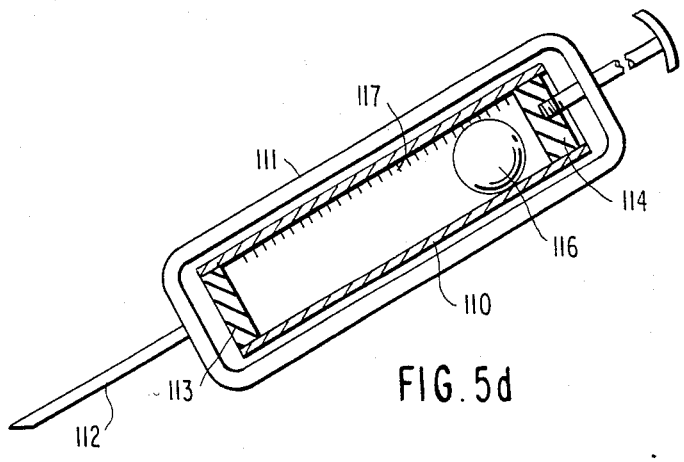

In the modification shown in FIG. 5d, the tube 110 is of the type used for extracting and sending blood samples to laboratories for routine blood analysis. Such tubes are placed in holder frames 111 having a needle 112 therein. A rubber or neoprene seal 113 in the end of the tube is penetrated by a punch (not shown) in the frame 111 and the piston 114 withdrawn to draw the sample. The tube is removed from the frame and forwarded to a blood laboratory for analysis. According to this invention, a weight member, such as stainless steel ball 116 is carried in tube 110 and the time it takes for the ball to fall through a predetermined volume of blood is measured by a stop watch and thus is a measure of the viscosity of the blood sample in tube 110. This information is noted on the patient's chart and on the tube forwarded to the laboratory where it can be used in the chemical analysis of the patient's blood and otherwise used in diagnosing the patient's condition.

While I have shown and described preferred embodiments of my invention and have suggested other embodiments and modifications, it will be apparent that other embodiments and modifications will be apparent to those skilled in the art and it is intended that such be encompassed by the spirit and scope of the claims appended hereto.

What is claimed is:

1. Blood viscosity measuring apparatus comprising in combination,
   a hypodermic syringe for withdrawing a predetermined quantity of blood from a living body, said hypodermic syringe having a needle for entering a patient's body, a hypodermic plunger piston and a hollow body member for receiving said predetermined quantity of a patient's blood,
   weight member in said hollow body member, said weight member having at least one elongated passageway therein adapted to permit said predetermined quantity of blood to relatively move from one known position in said hollow body member to another position through said at least one elongated passageway at a rate determined by the viscosity of said blood,
   said elongated passageway being defined by constricted passageway means formed in said hypodermic plunger piston, and check valve means for sealing said constricted passageway during the withdrawal of blood from said patient's body and permitting blood to flow through said constricted passageway during relative flow of said blood between said positions
   timer means,
   means for starting said timer means when said predetermined quantity of blood is at said one known position and stopping said timer means when said predetermined quantity of blood is at said another position,
   display means for displaying the time of relative movement of said predetermined quantity of blood between said positions as a measure of the viscosity of said blood from said patient's body.

2. The invention defined in claim 1 including a means for supporting said hypodermic syringe in a vertical orientation to permit said weight to move causing said relative flow of blood between said positions.

3. Apparatus for measuring the viscosity of blood comprising,
   a hypodermic syringe including a transparent hollow tube, a hollow hypodermic needle secured to one end of said transparent hollow tube with a passage in said needle communicating with the interior of said tube, plunger means in said hollow tube for creating a vacuum for extracting a predetermined volume of blood and passing same to the interior of said transparent hollow tube,
   means for maintaining said syringe at about the normal human body temperature,
   a constricted elongated passage in said transparent hollow tube,
   means for causing relative flow of a predetermined quantity of blood through said constricted elongated passage by gravity at a rate which is a function of the viscosity of said blood in said transparent hollow tube, and
   means for indicating the time of movement of said predetermined quantity of blood through said constricted elongated passageway as a measure of the viscosity of the blood in said transparent hollow tube.

4. The invention defined in claim 3 wherein said constricted elongated passageway divides said hollow chamber into two portions, and a fluid pressure equalizing coupling between said two portions.

5. The invention defined in claim 1 including a check valve means associated with said elongated passageway in said weight member to permit blood to flow freely in a unidirectional manner with respect to said weight member.

6. The invention defined in claim 5 wherein said hollow tube has interior sides and said check valve member is a flexible Teflon and engages and seals with said interior sides of said hollow tube.

7. The invention defined in claim 1 including a hollow operating handle and means securing said hollow operating handle to said weight with the interior of said hollow handle communicating with the blood in said hollow tube whereby the level of blood in said hollow handle is a measure of the pressure on said blood and the rate of travel of said weight and handle is a measure of the viscosity of said blood.

8. A method of measuring the viscosity of a patient's blood, comprising,
 (a) maintaining a hollow body of a syringe at substantially the temperature of said patient,
 (b) withdrawing a predetermined quantity of blood from the body of a patient by said syringe having a needle leading to a chamber in said hollow body for storing said predetermined quantity of blood,
 (c) and, immediately measuring the viscosity of said blood while it is in said chamber by causing the blood to flow through an elongated constricted passageway contained in said chamber.

9. The method defined in claim 8 wherein said elongated passageway is formed in a weight member which is movable by gravity between a pair of known positions in said hollow chamber.

10. The method defined in claim 9 wherein said elongated passageway is stationary and partitions said chamber into two portions, causing the blood to flow from one chamber portion to the other chamber portion by inverting said hollow body after storing said predetermined quantity of blood.

* * * * *